US00PP19080P2

(12) United States Plant Patent
Talmadge

(10) Patent No.: US PP19,080 P2
(45) Date of Patent: Aug. 5, 2008

(54) ***SUTERA* PLANT NAMED 'BALABOWITE'**

(50) Latin Name: *Sutera grandiflora*
Varietal Denomination: Balabowite

(75) Inventor: Paul A. Talmadge, Orcutt, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/823,339

(22) Filed: Jun. 27, 2007

(51) Int. Cl.
*A01H 5/00* (2006.01)

(52) U.S. Cl. ..... Plt./485

(58) Field of Classification Search ..... Plt./485
See application file for complete search history.

(56) References Cited

U.S. PATENT DOCUMENTS

PP17,897 P2 * 8/2007 Fick ..... Plt./485

OTHER PUBLICATIONS

Canada Plant Breeders' Rights application No. 07–5881 filed Apr. 12, 2007—not published when this IDS was prepared.

* cited by examiner

*Primary Examiner*—Wendy C. Haas
(74) *Attorney, Agent, or Firm*—Audrey Charles

(57) ABSTRACT

A new and distinct cultivar of *Sutera* plant named 'Balabowite', characterized by its single type white-colored flowers, dark green-colored foliage, and moderately vigorous, spreading and trailing growth habit.

1 Drawing Sheet

Latin name of genus and species of plant claimed: *Sutera grandiflora.*
Variety denomination: 'Balabowite'.

BACKGROUND OF THE INVENTION

The present invention relates to a new and distinct cultivar of *Sutera* plant botanically known as *Sutera grandiflora* and hereinafter referred to by the cultivar name 'Balabowite'.

The new cultivar originated in a controlled breeding program in Guadalupe, Calif. during October 2003. The objective of the breeding program was the development of Sutera cultivars that continuously flower with attractive flower coloration, dark green-colored foliage, excellent basal branching, and spreading growth habit.

The new *Sutera* cultivar is the result of cross-pollination. The female (seed) parent of the new cultivar is the proprietary *Sutera grandiflora* breeding selection designated 25358-1, not patented, characterized by its single type white-colored flowers, dark green-colored foliage, and prostrate and trailing growth habit. The male (pollen) parent of the new cultivar is the proprietary *Sutera grandiflora* breeding selection designated 6472-6475ml-1, not patented, characterized by its single type length lavender-colored flowers, medium green-colored foliage, and semi-upright and trailing growth habit. The new cultivar was discovered and selected as a single flowering plant within the progeny of the above stated cross-pollination during June 2004 in a controlled environment at Guadalupe, Calf.

Asexual reproduction of the new cultivar by terminal stem cuttings since June 2004 at Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar has been repeatedly observed and can be used to distinguish 'Balabowite' as a new and distinct cultivar of *Sutera* plant:

1. Single type, white-colored flowers;
2. Dark green-colored foliage; and
3. Moderately vigorous, spreading and trailing growth habit.

Plants of the new cultivar differ from plants of the female parent primarily in flower size, leaf size, and growth habit and from plants of the male parent primarily in flower color, flower size, leaf size, and foliage color.

Of the many commercially available *Sutera* cultivars, the most similar in comparison to the new cultivar is Abunda™ Giant White 'Blisch' U.S. Plant Pat. No. 17,082. However, in side by side comparisons, plants of the new cultivar differ from plants of 'Blisch' in the following characteristics:

1. Plants of the new cultivar have fewer flowers than plants of 'Blisch'; and
2. Plants of the new cultivar have a slightly darker leaf color than plants of 'Blisch'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balabowite'. The plants were grown in 4.5 inch pots for 9 weeks in a greenhouse at West Chicago, Ill.

DETAILED BOTANICAL DESCRIPTION

Figure 1:
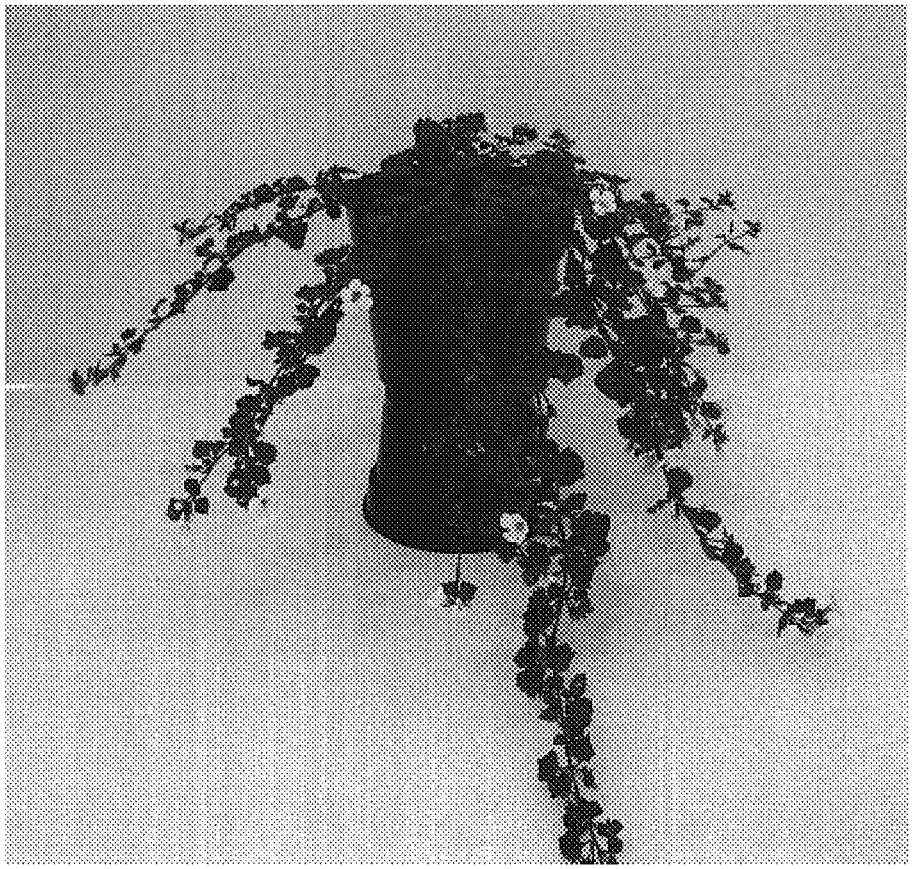
FIG. 1 illustrates a side view of the overall growth and flowering habit of 'Balabowite'.
Figure 2:
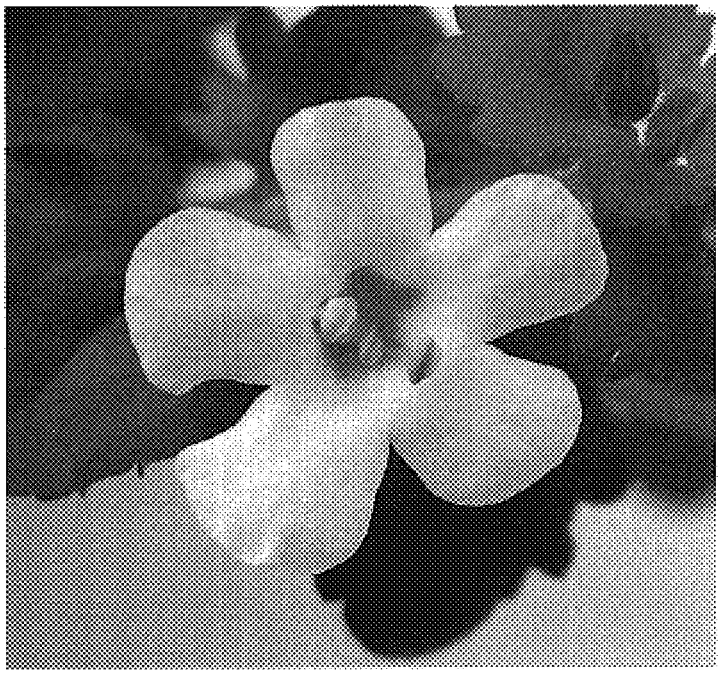
FIG. 2 illustrates a close-up view of an individual flower of 'Balabowite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 9, 2007 between 1:00 p.m. and 3:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Sutera grandiflora* cultivar Balabowite.

Parentage:

*Female parent.*—Proprietary *Sutera grandiflora* breeding selection designated 25358-1, not patented.

*Male parent.*—Proprietary *Sutera grandiflora* breeding selection designated 6472-6475ml-1, not patented.

Propagation:

*Type cutting.*—Terminal stem.

*Time to initiate roots.*—Approximately 10 to 13 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, spreading, trailing.

*Size.*—Height from soil level to top of plant plane: Approximately 4.7 cm. Width: Approximately 59.3 cm.

*Branching habit.*—Freely branching. Pinching will improve basal branching. Quantity of main branches per plant: Approximately 6.

*Branch.*—Strength: Strong. Length: Approximately 32.8 cm. Diameter: Approximately 2.0 mm. Length of central internode: Approximately 2.5 cm. Texture: Densely pubescent. Color of young and mature stems: 144A.

Foliage description:

*General description.*—Quantity of leaves per main branch: Approximately 26. Fragrance: None. Form: Simple. Arrangement: Opposite.

*Leaves.*—Aspect: Acute angle to stem; leaf blade transitions to an obtuse angle to stem with age. Shape: Broadly ovate. Margin: Serrate. Apex: Acute. Base: Attenuate, Venation pattern: Pinnate. Length of mature leaf: Approximately 1.6 cm. Width of mature leaf: Approximately 1.9 cm. Texture of upper and lower surfaces: Sparsely pubescent. Color of upper surface of young foliage: Closest to 139A with indistinguishable venation. Color of lower surface of young and mature foliage: 137C with venation of 137D. Color of upper surface of mature foliage: Darker than 137A with indistinguishable venation.

*Petiole.*—Length: Approximately 5.3 mm. Diameter: Approximately 1.0 mm. Texture: Sparsely pubescent. Color: 137D.

Flowering description:

*Flowering habit.*—'Balabowite' is freely flowering under outdoor growing conditions with substantially continuous blooming from spring through autumn and year-round in greenhouse environment.

*Lastingness of individual flower on the plant.*—Approximately 6 to 9 days.

Flower description:

*General description.*—Type: Solitary, axillary, salverform and persistent. Quantity per plant: Approximately 19. Fragrance: None.

*Bud.*—Rate of opening: Generally takes 1 to 2 days for bud to progress from first color to fully open flower. Quantity per plant: Approximately 10.

*Bud just before opening.*—Shape: Obovoid. Length: Approximately 6.6 mm. Diameter: Approximately 3.0 mm. Texture: Densely glandular pubescent. Gland color: Colorless, transparent. Color: 155D.

*Corolla.*—Diameter: Approximately 1.7 cm.

*Petals.*—Quantity: 5, fused to form a tube. Shape: Obovate. Margin: Entire. Apex: Obtuse. Length from tube: Approximately 7.1 mm. Length of free portion: Approximately 6.1 mm. Width: Approximately 6.8 mm. Texture of upper and lower surfaces: Glabrous. Color of upper surface when first and fully open: Purer white than 155D. Color of lower surface when first and fully open: Purer white than 155D.

*Corolla tube.*—Length: Approximately 1.1 cm. Diameter at distal end: Approximately 3.0 mm. Diameter at proximal end: Approximately 1.0 mm. Texture of inner surface: Densely pubescent. Texture of outer surface: Densely glandular pubescent. Gland color: Colorless, transparent. Color of inner surface: 25A and throat of 12A. Color of outer surface: 191C with an overlay of 163B at distal end.

*Peduncle.*—Strength: Strong. Aspect: Acute angle to stem. Length: Approximately 3.4 mm. Diameter: Less than 1 mm. Texture: Densely pubescent. Color: 144A.

*Sepals.*—Quantity per flower: 5, fused at base. Shape: Narrow linear. Apex: Acute. Length: Approximately 5.0 mm. Width: Approximately 1.0 mm. Texture of upper surface: Sparsely pubescent. Texture of lower surface: Densely pubescent. Color of upper surface: 137A. Color of lower surface: 144A at base transitioning to 137A toward apex.

*Reproductive organs.*—Androecium: Stamen quantity: 4 didynamous, basifixed. Stamen length of longer pair: Approximately 1.0 cm. Filament length of free portion of longer pair: Approximately 4.0 cm. Stamen length of shorter pair: Approximately 8.0 mm. Filament length of free portion of shorter pair: Approximately 2.0 mm. Filament color: Purer white than 155D. Anther shape: Funnel. Anther length: Less than 1 mm. Anther color: 22A. Pollen amount:

Scarce. Pollen color: 21C. Gynoecium: Pistil quantity: 1 per flower. Pistil length: Approximately 1.0 cm. Stigma shape: Elongated, curved. Stigma length: Approximately 1.0 mm. Stigma color: 144A. Style length: Approximately 8.0 mm. Style color: 155D. Ovary length: Approximately 1.0 mm. Ovary color: 144A.

Seed and fruit production: Neither seed nor fruit production has been observed.

Disease and pest resistance: Resistance to pathogens and pests common to *Sutera* has not been observed.

What is claimed is:

1. A new and distinct cultivar of *Sutera* plant named 'Balabowite', substantially as herein shown and described.

* * * * *